United States Patent
Teshigahara et al.

(10) Patent No.: US 7,132,384 B2
(45) Date of Patent: Nov. 7, 2006

(54) PROCESS FOR PRODUCING COMPOSITE OXIDE CATALYST

(75) Inventors: Isao Teshigahara, Mie (JP); Nariyasu Kanuka, Mie (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/044,187

(22) Filed: Jan. 28, 2005

(65) Prior Publication Data

US 2005/0131253 A1    Jun. 16, 2005

Related U.S. Application Data

(63) Continuation of application No. PCT/JP04/15635, filed on Oct. 21, 2004.

(30) Foreign Application Priority Data

Nov. 14, 2003  (JP) ............................... 2003-385756

(51) Int. Cl.
*B01J 21/18* (2006.01)
*B01J 23/00* (2006.01)
*B01J 23/58* (2006.01)
*B01J 23/70* (2006.01)
*C07C 51/16* (2006.01)

(52) U.S. Cl. ...................... 502/182; 502/311; 502/330; 502/337; 502/338; 562/546; 562/547

(58) Field of Classification Search .............. 502/182, 502/311–321, 330, 337, 338; 562/546, 547
See application file for complete search history.

(56) References Cited

U.S. PATENT DOCUMENTS 3,761,424 A * 9/1973 Koberstein et al. ......... 502/212
4,052,450 A * 10/1977 Krabetz et al. ............. 562/546
2004/0054222 A1* 3/2004 Felder et al. ................ 562/547

FOREIGN PATENT DOCUMENTS

| JP | 56-97 | 1/1981 |
|---|---|---|
| JP | 56-23969 | 6/1981 |
| JP | 56-161841 | 12/1981 |
| JP | 60-150834 | 8/1985 |
| JP | 2-55103 | 11/1990 |
| JP | 6-374 | 1/1994 |
| JP | 7-16463 | 1/1995 |
| JP | 2002-539101 | 11/2002 |
| JP | 2003-305367 | 10/2003 |

* cited by examiner

*Primary Examiner*—David Sample
*Assistant Examiner*—Patricia L. Hailey
(74) *Attorney, Agent, or Firm*—Oblon, Spivak, McClelland, Maier & Neustadt, P.C.

(57) ABSTRACT

A process for producing a composite oxide catalyst to be used for gas phase oxidation of an olefin or unsaturated aldehyde with molecular oxygen to produce the corresponding unsaturated aldehyde and/or unsaturated carboxylic acid, which has a uniform constant high performance, in an industrial scale and efficiently and constantly, is presented.

The process comprises a step of molding a catalyst component-containing powder and a step of calcining a molded product obtained in the molding step, wherein the molding step is a step wherein graphite particles having an average particle diameter $D_{50}$ of from 10 to 50 μm and having a combustion initiating temperature in a differential thermogravimetric analysis higher by at least 50° C. than the calcination temperature in the next calcination step, are added to the catalyst component-containing powder in an amount of from 0.5 to 10 wt %, based on the powder, followed by molding, and the calcination step is a step wherein the calcination is carried out at a temperature of at least 250° C. and lower by at least 50° C. than the combustion initiating temperature of the graphite particles.

12 Claims, No Drawings

PROCESS FOR PRODUCING COMPOSITE OXIDE CATALYST

TECHNICAL FIELD

The present invention relates to a process for producing a composite oxide catalyst to be used for gas phase oxidation of an olefin or unsaturated aldehyde to produce the corresponding unsaturated aldehyde and/or unsaturated carboxylic acid. More particularly, the olefin is propylene or isobutylene, and the unsaturated aldehyde is acrolein or methacrolein, and the present invention relates to a process for producing a composite oxide catalyst to be used for producing from such an olefin or unsaturated aldehyde the corresponding acrolein or methacrolein, and/or acrylic acid or methacrylic acid.

BACKGROUND ART

Heretofore, various proposals have been made with respect to composite oxide catalysts for gas phase catalytic oxidation of propylene or isobutylene with molecular oxygen to produce acrolein and acrylic acid, or methacrolein and methacrylic acid. Specifically, patent Document 1 may be mentioned.

Further, various proposals have, heretofore, been made also with respect to composite oxide catalysts for gas phase oxidation of acrolein or methacrolein to produce acrylic acid or methacrylic acid. Specifically, patent Document 2 may, for example, be mentioned.

In the production of such composite oxide catalysts in a large industrial scale, the method for molding the catalyst component-containing mixture and the method for calcination (heat treatment) will give substantial influences not only on the physical properties of the catalysts to be thereby produced but also on the catalytic performance.

Therefore, heretofore, various proposals have been made also with respect to the molding method and the calcination method for the composite oxide catalysts. For example, patent Document 3 discloses a molding assistant and molding conditions to be used for extrusion molding, and patent Document 4 discloses that an activated carbon powder having a specific particle diameter is effective as a molding assistant. Further, also with respect to the calcination method, e.g. patent Document 5 discloses thermal decomposition conditions.

Patent Document 1: JP-B-56-23969
Patent Document 2: JP-B-56-97
Patent Document 3: JP-A-7-16463
Patent Document 4: JP-A-6-374
Patent Document 5: JP-B-2-55103

DISCLOSURE OF THE INVENTION

Problem to be Solved by the Invention

However, the conventional techniques for producing composite oxide catalysts are based on the production in a laboratory scale, and it can hardly be said that adequate studies have been made with respect to the industrial production, particularly with respect to the molding and calcination of the catalysts. Consequently, there have been drawbacks such that no adequate productivity has been obtained, non-uniformity or instability has resulted in the catalytic performance, and further, the catalytic performance itself has been impaired.

Under these circumstances, it is an object of the present invention to provide a process for producing a composite oxide catalyst to be used for gas phase oxidation of an olefin or unsaturated aldehyde with molecular oxygen to produce the corresponding unsaturated aldehyde and/or unsaturated carboxylic acid, whereby a catalyst having a uniform constant high performance can be produced in an industrial scale efficiently and constantly.

Means to Solve the Problem

The present inventors have conducted an extensive research to accomplish the above object and have found that in a composite oxide catalyst to be used for gas phase oxidation of an olefin or unsaturated aldehyde to produce the corresponding unsaturated aldehyde and/or unsaturated carboxylic acid, by using graphite having a specific nature as a molding assistant and by employing a temperature within a specific range as the temperature in the calcination step, it becomes possible to improve the productivity in the molding step, to stabilize the catalytic performance and to facilitate control of the heat treatment in the calcination step, and it becomes possible to produce a high performance catalyst in an industrial scale efficiently and constantly, and thus, they have arrived at the present invention.

Thus, the present invention is characterized by the following constructions.

(1) A process for producing a composite oxide catalyst to be used for gas phase oxidation of an olefin or unsaturated aldehyde with molecular oxygen to produce the corresponding unsaturated aldehyde and/or unsaturated carboxylic acid, which comprises a step of molding a catalyst component-containing powder and a step of calcining a molded product obtained in the molding step, wherein:

the molding step is a step wherein graphite particles having an average particle diameter $D_{50}$ of from 10 to 50 µm and having a combustion initiating temperature in a differential thermogravimetric analysis higher by at least 50° C. than the calcination temperature in the next calcination step, are added to the catalyst component-containing powder in an amount of from 0.5 to 10 wt %, based on the powder, followed by molding, and the calcination step is a step wherein the calcination is carried out at a temperature of at least 250° C. and lower by at least 50° C. than the combustion initiating temperature of the graphite particles.

(2) The process for producing a composite oxide catalyst according to the above (1), wherein the composite oxide catalyst is a catalyst for producing from an olefin the corresponding unsaturated aldehyde and/or unsaturated carboxylic acid, and contains at least Mo, Bi and Fe as its component elements.

(3) The process for producing a composite oxide catalyst according to the above (2), wherein the composite oxide catalyst has the formula MoaBibCocNidFeeXfYgZhQiSijOk (wherein X represents at least one element selected from the group consisting of Na, K, Rb, Cs and Tl, Y represents at least one element selected from the group consisting of B, P, As and W, Z represents at least one element selected from the group consisting of Mg, Ca, Zn, Ce and Sm, Q represents a halogen atom, and a to k represent atomic ratios of the respective elements, and when a is 12, b is from 0.5 to 7, c is from 0 to 10, d is from 0 to 10, c+d is from 0 to 10, e is from 0.05 to 3, f is from 0.0005 to 3, g is from 0 to 3, h is from 0 to 1, i is from 0 to 0.5 and j is from 0 to 40, and k is a numerical value which satisfies the oxidized states of other elements.)

(4) The process for producing a composite oxide catalyst according to the above (1), wherein the composite oxide catalyst is a catalyst for producing from an unsaturated aldehyde the corresponding unsaturated carboxylic acid, and contains at least Mo and V as its component elements.

(5) The process for producing a composite oxide catalyst according to the above (4), wherein the composite oxide catalyst has the formula $Mo_aV_bCu_cX_dY_eZ_fO_g$ (wherein X represents at least one element selected from the group consisting of W and Nb, Y represents at least one element selected from the group consisting of Fe, Co, Ni and Bi, Z represents at least one element selected from the group consisting of Ti, Zr, Ce, Cr, Mn, Sb and Si, and a, b, c, d, e, f and g represent atomic ratios of the respective elements, and when a is 12, b is from 1 to 12, c is from 0 to 6, d is from 0 to 12, e is from 0 to 100, f is from 0 to 100, and g is a numerical value determined by the oxidized states of the respective elements.)

(6) A method which comprises contacting an olefin with molecular oxygen in the presence of the composite oxide catalyst as defined in the above (2) or (3) for gas phase oxidation to produce the corresponding unsaturated aldehyde and/or unsaturated carboxylic acid.

(7) The method according to the above (6), wherein the olefin is propylene, and the unsaturated aldehyde and unsaturated carboxylic acid are acrolein and acrylic acid, respectively.

(8) A method which comprises contacting an unsaturated aldehyde with molecular oxygen in the presence of the composite oxide catalyst as defined in the above (4) or (5) for gas phase oxidation to produce the corresponding unsaturated carboxylic acid.

(9) The method according to the above (8), wherein the unsaturated aldehyde is acrolein, and the unsaturated carboxylic acid is acrylic acid.

EFFECTS OF THE INVENTION

In the process for producing a composite oxide catalyst of the present invention, graphite having a specific nature is used as a molding assistant, and a temperature within a specific range is employed as the temperature in the calcination step, whereby it becomes possible to improve the productivity in the molding step, to stabilize the catalytic performance and to facilitate control of the heat treatment in the calcination step, and a high performance catalyst can be produced in an industrial scale efficiently and constantly.

BEST MODE FOR CARRYING OUT THE INVENTION

The composite oxide catalyst to be produced by the present invention, is a catalyst to be used for producing an unsaturated aldehyde and/or an unsaturated carboxylic acid from an olefin, or a catalyst to be used for producing an unsaturated carboxylic acid from an unsaturated aldehyde. In the present invention, the olefin is preferably propylene or isobutylene; the unsaturated aldehyde is preferably acrolein or methacrolein; and the unsaturated carboxylic acid is preferably acrylic acid or methacrylic acid. The present invention may particularly preferably be applied to produce a composite oxide catalyst to be used for producing acrolein and/or acrylic acid from propylene, or to produce a composite oxide catalyst to be used for producing acrylic acid from acrolein.

In the present invention, the composite oxide catalyst to be used for producing from an olefin the corresponding unsaturated aldehyde and/or unsaturated carboxylic acid, is preferably a catalyst which contains at least Mo, Bi and Fe as its component elements. Such a composite oxide catalyst is preferably one having the formula $Mo_aBi_bCo_cNi_dFe_eX_fY_gZ_hQ_iSi_jO_k$ (wherein Mo represents molybdenum, Bi represents bismuth, Co represents cobalt, Ni represents nickel, Fe represents iron, Si represents silicon and O represents oxygen, X represents at least one element selected from the group consisting of Na, K, Rb, Cs and Tl, Y represents at least one element selected from the group consisting of B, P, As and W, Z represents at least one element selected from the group consisting of Mg, Ca, Zn, Ce and Sm, Q represents a halogen atom, and a to k represent atomic ratios of the respective elements, and when a is 12, b is from 0.5 to 7, c is from 0 to 10, d is from 0 to 10, c+d is from 0 to 10, e is from 0.05 to 3, f is from 0.0005 to 3, g is from 0 to 3, h is from 0 to 1, i is from 0 to 0.5 and j is from 0 to 40, and k is a numerical value which satisfies the oxidized states of other elements.)

Further, in the present invention, the composite oxide catalyst to be used for producing from an unsaturated aldehyde the corresponding unsaturated aldehyde and/or unsaturated carboxylic acid, is preferably a catalyst which contains at least Mo and V as its component elements. Such a composite oxide catalyst is preferably one having the formula $Mo_aV_bCu_cX_dY_eZ_fO_g$ (wherein Mo represents molybdenum, V represents vanadium, Cu represents copper, and O represents oxygen, X represents at least one element selected from the group consisting of W and Nb, Y represents at least one element selected from the group consisting of Fe, Co, Ni and Bi, Z represents at least one element selected from the group consisting of Ti, Zr, Ce, Cr, Mn, Sb and Si, and a, b, c, d, e, f and g represent atomic ratios of the respective elements, and when a is 12, b is from 1 to 12, c is from 0 to 6, d is from 0 to 12, e is from 0 to 100, f is from 0 to 100, and g is a numerical value determined by the oxidized states of the respective elements.)

In the present invention, raw material compounds for the respective component elements to be used for producing a composite oxide catalyst, are not particularly limited so long as they are compounds capable of being converted to oxides in the subsequent calcination step. Further, the raw material compounds for the respective component elements mean not only compounds containing the respective elements individually, but also a compound containing a plurality of elements commonly (for example, ammonium phosphorus molybdate containing Mo and P). The raw material compounds of the respective component elements may, for example, be oxides, nitrates, carbonates, ammonium salts, hydroxides, carboxylates, ammonium carboxylates or halogenated ammonium salts, of the component elements.

The following may be mentioned as specific examples of the raw material compounds for the main component elements. Compounds containing Mo may, for example, be ammonium para-molybdate, molybdenum trioxide, molybdic acid, ammonium phosphorus molybdate and phosphorus molybdic acid. Compounds containing Bi may, for example, be bismuth chloride, bismuth nitrate, bismuth oxide and bismuth carbonate. Compounds containing Fe may, for example, be ferric nitrate, ferric sulfate, ferric chloride and ferric acetate. Compounds containing V may, for example, be ammonium metavanadate and vanadium trioxide.

In the production of a composite oxide catalyst, the raw material compounds for the respective component elements are usually used in their powder forms, and they are preferably dissolved or dispersed in a suitable medium such as water in the form of a uniform solution or slurry. To obtain such a uniform solution or slurry, the raw material compounds of all component elements may be dissolved or suspended all at once or successively. However, they may not necessarily be so treated, but a prescribed uniform solution or slurry may be preliminarily prepared in a separate step, so that it may be mixed with other uniform solutions or slurries. Otherwise, a prescribed uniform solution or slurry is preliminarily prepared in a separate step, and then dried and, if necessary, subjected to heat treatment, whereupon it may be mixed with other uniform solutions or slurries.

The uniform solution or aqueous slurry containing the component elements of the catalyst will then be dried. Here, the method or the state of the dried product thereby obtained is not particularly limited. For example, a dried product of a powder form may be obtained by means of e.g. a common spray dryer, slurry dryer or drum dryer, or a dried product of a block or flake shape may be obtained by means of a common box type dryer or tunnel type calcination furnace.

The dried powder product obtained in the drying step may be used as it is, as a catalyst component-containing powder to be subjected to a molding step, but for the purpose of preliminary decomposition, this dried powder may further be subjected to heat treatment and then used as a catalyst component-containing powder. Such heat treatment is carried out at a temperature of from 200 to 400° C. The means for the heat treatment is not particularly limited, but industrially, it is preferred to use a rotary kiln from the viewpoint of the uniform stability of the heat treatment and the continuous productivity.

The dried catalyst component-containing powder thus obtained, is then molded into a desired shape in a molding step. The molding assistant to be used in the molding step is not only substantially influential over the properties of the molded product obtained in the molding step but also substantially influential over the calcination step as the next step. For example, in a case where a combustible molding assistant is substantially contained, an abrupt combustion reaction is likely to occur during the calcination step, whereby the catalyst is likely to be exposed to a temperature higher than necessary or oxidized more than necessary, and in some cases, it may be reduced. Consequently, the surface or bulk structure of the catalyst may be changed; the catalytic performance itself may be impaired; the constant stability may be lost; or the physical property of the catalyst such as mechanical strength may be influenced. Such influences may substantially be negligible in the preparation of a catalyst in a laboratory scale i.e. a scale of a few tens grams, but they will be a serious problem in the production of the catalyst in an industrial scale.

In a case where it is attempted to solve the above mentioned problem in the calcination step, the calcination apparatus tends to be complex and large-sized, or the operation tends to be cumbersome or take a long time, such being economically disadvantageous.

In the present invention, graphite having a specific nature is used as a molding assistant, based on a recognition such that it is important to properly select the molding assistant in order to solve such problems. Graphite has a structure wherein large carbon hexagonal planes are regularly laminated in more than a few hundreds layers, and many types are present which are different in the lamination structures. Broadly, they are classified into natural graphite and artificial graphite. Graphite is used for various applications such as carbon electrodes, resin additives, lubricants or packing materials. In the present invention, among such various graphites, one having a combustion initiation temperature (which is also called a weight reduction and heat generation initiation temperature and will hereinafter be referred to also as Tburn) in a differential thermogravimetric analysis higher by at least 50° C. than the calcination temperature (hereinafter referred to also as Tcal.) in the next calcination step, is used. Further, the graphite is required to be graphite particles having an average particle diameter $D_{50}$ of from 10 to 50 µm.

If the combustion initiation temperature of the graphite as the molding assistant is not higher by at least 50° C. than the combustion temperature in the combustion step, when the molded product is calcined in the calcination step, particularly when it is calcined in a large industrial scale, depending upon the conditions such as the shape of the calcination installation, the flow rate of the calcination gas, the amount of graphite added, etc., abnormal heat generation is likely to result due to the combustion of graphite, and the production may tends to be unstable as the calcination scale increases. The combustion initiation temperature of the graphite is particularly preferably higher by at least 60° C. than the calcination temperature. The average particle diameter $D_{50}$ means a 50% particle diameter, based on mass in the particle size distribution measurement.

The graphite as a molding assistant is added the above catalyst component-containing powder in an amount of from 0.5 to 10 wt %, preferably from 0.8 to 5 wt %, based on the powder. When used in this range, the graphite will function as a lubricant, whereby the productivity in the molding step will be improved, and at the same time, calcination can be carried out constantly without need to worry about abnormal heat generation in the calcination step. On the other hand, if the amount of the graphite is less than 0.5%, the effect as a lubricant will not substantially be sufficient, and if molding is carried out continuously over a long time, creaking will occur, and disassembling and cleaning the molding machine will be required. If molding is continued while creaking continues, a component of the molding machine may be damaged. On the other hand, if the graphite exceeds 10 wt %, the strength of the tabletted catalyst tends to be low, such being not practical. As a molding assistant, in addition to the graphite, other adjuvants such as polyvinyl alcohol, carboxymethylcellulose, crystalline cellulose and in organic fiber such as carbon fiber, may also be used in combination. Such other adjuvants may be added to the above catalyst component-containing powder in an amount of preferably from 0 to 10 wt %, particularly preferably from 0 to 5 wt %, based on the powder.

The above catalyst component-containing powder is molded by a suitable molding machine such as a tabletting machine, an extrusion molding machine or a tumbling granulation machine. The shape of the molded product is not particularly limited, and an optional shape may be selected for use such as a spherical, ring, cylindrical, pellet or star-like shape. The size of the molded product is also optional, and the diameter or length is preferably at a level of from 3 to 10 mm.

The obtained molded product is then subjected to and calcined in the calcination step. The calcination temperature in this calcination step is preferably within a range of at least 250° C. and lower by at least 50° C. than the combustion initiation temperature of the graphite used as the molding assistant. Here, the calcination temperature in the present invention is the substantial temperature at which the molded product is calcined and a set temperature in the calcination step. If the calcination temperature is lower than 250° C., formation of active species tends to be inadequate, such being undesirable. Further, the calcination temperature is preferably within a range lower by at least 50° C. than the combustion initiation temperature of the graphite. Further, the calcination time is preferably from 1 to 50 hours, particularly preferably from 2 to 20 hours. By such calcination, in the present invention, a composite oxide catalyst having a uniform constant high performance can be produced with a high productivity.

The composite oxide catalyst according to the present invention may suitably be used for gas phase oxidation of an olefin or unsaturated aldehyde with molecular oxygen to produce the corresponding unsaturated aldehyde and/or unsaturated carboxylic acid, by a gas phase oxidation reaction using molecular oxygen, or molecular oxygen in a gas containing the molecular oxygen, such as air. As the apparatus and conditions for carrying out the gas phase oxidation reaction, those disclosed in the prior art references mentioned in the above background art may widely be used.

For example, in a case where an unsaturated aldehyde and/or unsaturated carboxylic acid is to be produced from an olefin, the molar ratio of olefin/molecular oxygen is preferably from 1/0.5 to 1/3. It is preferred to use the starting material olefin as diluted with an inert-gas. The reaction pressure is preferably from the atmospheric pressure to a few atms. The reaction temperature is preferably from 200 to 450° C., particularly preferably from 250 to 400° C. The reaction may be carried out either by a fixed bed or a fluidized bed.

Whereas, in a case where an unsaturated carboxylic acid is to be produced from an unsaturated aldehyde, the molar ratio of unsaturated aldehyde/molecular oxygen is preferably from 1/0.3 to 1/4. The starting material unsaturated aldehyde may contain a small amount of impurities such as water, a lower saturated aldehyde, etc. The unsaturated aldehyde may be diluted with an inert-gas such as nitrogen, steam or carbon dioxide. The reaction pressure is preferably from atmospheric pressure to a few atms. The reaction temperature is preferably from 200 to 400° C., particularly preferably from 220 to 350° C. The reaction may be carried out either by a fixed bed or a fluidized bed.

EXAMPLES

Now, the present invention will be described in further detail with reference to Examples of the present invention. However, it should be understood that the present invention is by no means restricted to such specific Examples. In the following Examples, the conversion of propylene, the selectivity, the yield, the conversion of acrolein, the selectivity for acrylic acid and the yield of acrylic acid are calculated by the following formulae.

Conversion of propylene (mol %): (mols of reacted propylene/mols of supplied propylene)×100

Selectivity (mol %): ((mols of formed acrolein+mols of formed acrylic acid)/mols of reacted propylene)×100

Yield (mol %): ((mols of formed acrolein+mols of formed acrylic acid)/mols of supplied propylene)×100

Conversion of acrolein (mol %): (mols of reacted acrolein/mols of supplied acrolein)×100

Selectivity for acrylic acid (mol %): (mols of formed acrylic acid/mols of reacted acrolein)×100

Yield of acrylic acid (mol %): (mols of formed acrylic acid/mols of supplied acrolein)×100

Example 1

107 g of ammonium paramolybdate was dissolved in 500 ml of warmed pure water. Then, 12.2 g of ferric nitrate, 38.2 g of cobalt nitrate and 58.8 g of nickel nitrate were dissolved in 100 ml of warmed pure water. These solutions were gradually mixed with thorough stirring. Then, 0.96 g of borax and 0.51 g of potassium nitrate were dissolved in 40 ml of pure water under heating and added to the above slurry.

Then, 72.9 g of silica was added, followed by thorough stirring. Then, 2.7 ml of nitric acid was added to 20 ml of water, and 24.5 g of bismuth nitrate was further added, followed by mixing with stirring. This slurry was dried at 130° C. and then subjected to heat treatment at 300° C. for one hour in an air atmosphere.

To the obtained granular solid, 4 wt %, based on the solid, of graphite particles (manufactured by NICHIDEN CARBON KK, combustion initiation temperature in the differential thermogravimetric analysis: 610° C., average particle diameter $D_{50}$: 31 μm, hereinafter referred to as "graphite 1") were added and thoroughly mixed, and then the mixture was molded into a cylindrical tablet having a diameter of 5 mm and a height of 4 mm by a tabletting machine. Continuous tabletting was free from a problem, and the strength of the obtained tabletted product was also constant.

Then, the tabletted product was put into a calcination vessel, heated to 525° C. over a period of four hours while circulating air at a space velocity (SV) of 260 $(hr^{-1})$ and then calcined by maintaining that temperature for 4 hours, to obtain a composite oxide catalyst. A thermocouple was inserted into the above calcination vessel, and the temperature distribution in the calcination vessel in the calcination state, was continuously measured. In the temperature rising process, heat generation at a level of 5° C. was ascertained, but no apparent heat generation was ascertained at the maintained temperature of 525° C.

The catalyst calculated from the charged raw materials is a composite oxide having the following atomic ratios.

Mo:Bi:Co:Ni:Fe:Na:B:K:Si=12:1:2.6:4:0.6:0.1:0.2:0.1:24

Further, 20 ml of this catalyst was packed into a stainless steel reaction tube equipped with a niter jacket and having an inter diameter of 15 mm, and a mixed gas comprising 8 mol % of propylene, 67 mol % of air and 25 mol % of steam, was introduced at a SV of 1500 $(hr^{-1})$, to carry out the oxidation reaction of propylene at a reaction bath temperature of 320° C. The results are as shown in Table 1.

Comparative Example 1

A catalyst was prepared in the same manner as in Example 1 except that graphite particles (manufactured by RAIMOND COMPANY, combustion initiation temperature in the differential thermogravimetric analysis: 540° C., average particle diameter $D_{50}$: 29 μm, hereinafter referred to as "graphite 2") were used as the graphite. There was no problem in the tabletting step. However, in the calcination step, combustion of graphite took place, and heat generation of about 200° C. was ascertained in the catalyst layer. The obtained catalyst had the strength decreased, and showed no catalytic activities.

Example 2

A catalyst was prepared in the same manner as in Example 1 except that the calcination temperature was changed to 545° C., and the SV of the calcination gas was changed to 50 $(hr^{-1})$, and the oxidation reaction of propylene was carried out. The results are shown in Table 1.

Example 3

A catalyst was prepared in the same manner as in Example 1 except that the amount of the graphite was changed to 1 wt %, and the oxidation reaction of propylene was carried out. The results are shown in Table 1.

Comparative Example 2

Molding of the catalyst was carried out in the same manner as in Example 1 except that the amount of the graphite was changed to 0.2 wt %, but creaking between the punch and the die was large, and it was not possible to carry out tabletting continuously. Therefore, it was impossible to carry out the oxidation reaction of propylene.

Comparative Example 3

Molding of the catalyst was carried out in the same manner as in Example 1 except that the amount of the graphite was changed to 15 wt %. The obtained molded catalyst had no adequate strength and cracked at the time of packing the catalyst. Thus, it was not practically useful, and no oxidation reaction of propylene was carried out.

This slurry was heated to from 80° C. to 100° C., concentrated and dried. This dried product was pulverized to at most 24 mesh. To this pulverized product, 1.5 wt %, based on the pulverized product, of the above mentioned graphite 2 was added, followed by thorough mixing. Then, it was molded into a columnar shape having a diameter of 5 mm and a height of 4 mm by a small size tabletting machine.

The obtained tabletted product was put into a 1 liter calcination vessel, and the calcination vessel was heated to 370° C. over a period of 3 hours while circulating nitrogen containing 1% of oxygen, followed by calcination for 4 hours at that temperature, to obtain a composite oxide catalyst. A thermo-couple was inserted into the calcination vessel, and the temperature distribution in the calcination vessel was continuously measured in a calcination state, whereby no apparent heat generation was ascertained. The catalyst calculated from the charged raw materials is a composite oxide having the following atomic ratios.

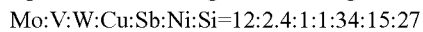

Mo:V:W:Cu:Sb:Ni:Si=12:2.4:1:1:34:15:27

30 ml of the obtained composite oxide catalyst was packed into a stainless steel reaction tube equipped with a niter jacket and having an inner diameter of 15 ml, and a starting material gas comprising 4% of acrolein, 46% of

TABLE 1

| | Molding step | | | Calcination step | | | Difference | Catalytic performance | | | |
|---|---|---|---|---|---|---|---|---|---|---|---|
| | graphite | | | | | heat | between | Conversion | | | |
| | Type | Tburn (° C.) | Amount (%) | Tcal (° C.) | SV (/hr) | generation (° C.) | Tburn and Tcal (° C.) | of propylene (%) | Selectivity (%) | Yield (%) | Notes |
| Examples | | | | | | | | | | | |
| 1 | Graphite 1 | 610 | 4 | 525 | 260 | 5 | 85 | 97.9 | 95.3 | 93.3 | |
| 2 | Graphite 1 | 610 | 4 | 545 | 50 | 4 | 65 | 96.8 | 95.5 | 92.4 | |
| 3 | Graphite 1 | 610 | 1 | 525 | 260 | 2 | 85 | 98.1 | 94.9 | 93.1 | |
| Comparative Examples | | | | | | | | | | | |
| 1 | Graphite 2 | 540 | 4 | 525 | 260 | 200 | 15 | 0 | 0 | 0 | |
| 2 | Graphite 1 | 610 | 0.2 | — | — | — | — | — | — | — | Molding failure |
| 3 | Graphite 1 | 610 | 15 | — | — | — | — | — | — | — | Molding failure |

Example 4

228 g of basic nickel carbonate ($NiCO_3 \cdot 2Ni(OH)_2 \cdot 4H_2O$) was dispersed in 300 ml of pure water. Then, 50 g of silica ("CARPLEX#67", manufactured by SHIONOGI & CO., LTD.) and 150 g of antimony trioxide were added thereto, followed by thorough stirring.

This slurry was heated, concentrated and dried. Then, the obtained solid was quickly put into a muffle furnace which was preliminarily maintained at 600° C., and heated to 800° C. over a period of 3 hours, followed by calcination at 800° C. for 3 hours. The calcined product was pulverized to obtain a (Sb—Ni—Si—O) powder having a diameter of at most 60 mesh.

540 ml of pure water was heated to about 80° C., and 8.1 g of ammonium paratungstate, 63.9 g of ammonium paramolybdate, 8.4 g of ammonium metavanadate and 2.8 g of cuprous chloride were sequentially added and dissolved with stirring. To the obtained solution, the above Sb—Ni—Si—O powder was added, followed by thorough stirring and mixing.

steam and 50% of air was passed at a SV of 1000 ($hr^{-1}$), to carry out a catalytic oxidation reaction of acrolein at a reaction bath temperature of 260° C.

As a result, the conversion of acrolein was 99.1%, the selectivity for acrylic acid was 95.6%, and the yield of acrylic acid was 94.7%.

The entire disclosure of Japanese Patent Application No. 2003-385756 filed on Nov. 14, 2003 including specification, claims and summary is incorporated herein by reference in its entirety.

What is claimed is:

1. A process for producing a composite oxide catalyst to be used for gas phase oxidation of an olefin or unsaturated aldehyde with molecular oxygen to produce the corresponding unsaturated aldehyde and/or unsaturated carboxylic acid, which comprises molding a catalyst component-containing powder and calcining a molded product obtained in the molding step, wherein:

said molding comprises adding graphite particles having a combustion initiating temperature in a differential thermogravimetric analysis higher by at least 50° C. than the calcination temperature in the next calcination step to the catalyst component-containing powder in an amount of from 0.5 to 10 wt %, based on the powder, followed by molding, and said calcining is conducted at a temperature of at least 250° C. and, wherein said temperature is lower by at least 50° C. than the combustion initiating temperature of the graphite particles.

2. The process for producing a composite oxide catalyst according to claim 1, wherein the composite oxide catalyst is a catalyst for producing from an olefin the corresponding unsaturated aldehyde and/or unsaturated carboxylic acid, and contains at least Mo, Bi and Fe as its component elements.

3. The process for producing a composite oxide catalyst according to claim 2, wherein the composite oxide catalyst has the formula $Mo_aBi_bCo_cNi_dFe_eX_fY_gZ_hQ_iSi_jO_k$, wherein X represents at least one element selected from the group consisting of Na, K, Rb, Cs and Tl, Y represents at least one element selected from the group consisting of B, P, As and W, Z represents at least one element selected from the group consisting of Mg, Ca, Zn, Ce and Sm, Q represents a halogen atom, and a to k represent atomic ratios of the respective elements, with the proviso that when a is 12, b is from 0.5 to 7, c is from 0 to 10, d is from 0 to 10, c+d is from 0 to 10, e is from 0.05 to 3, f is from 0.0005 to 3, g is from 0 to 3, h is from 0 to 1, i is from 0 to 0.5 and j is from 0 to 40, and k is a numerical value which satisfies the oxidized states of other elements.

4. A method which comprises contacting an olefin with molecular oxygen in the presence of the composite oxide catalyst obtained by the process as defined in claim 2 for gas phase oxidation to produce the corresponding unsaturated aldehyde and/or unsaturated carboxylic acid.

5. The method according to claim 4, wherein the olefin is propylene, and the unsaturated aldehyde and unsaturated carboxylic acid are acrolein and acrylic acid, respectively.

6. The method according to claim 4, wherein the wherein the composite oxide catalyst has the formula $Mo_aBi_bCo_cNi_dFe_eX_fY_gZ_hQ_iSi_jO_k$, wherein X represents at least one element selected from the group consisting of Na, K, Rb, Cs and Tl, Y represents at least one element selected from the group consisting of B, P, As and W, Z represents at least one element selected from the group consisting of Mg, Ca, Zn, Ce and Sm, Q represents a halogen atom, and a to k represent atomic ratios of the respective elements, with the proviso that when a is 12, b is from 0.5 to 7, c is from 0 to 10, d is from 0 to 10, c+d is from 0 to 10, e is from 0.05 to 3, is from 0.0005 to 3, g is from 0 to 3, h is from 0 to 1, i is from 0 to 0.5 and j is from 0 to 40, and k is a numerical value which satisfies the oxidized states of other elements.

7. The process for producing a composite oxide catalyst according to claim 1, wherein the composite oxide catalyst is a catalyst for producing from an unsaturated aldehyde the corresponding unsaturated carboxylic acid, and contains at least Mo and V as its component elements.

8. The process for producing a composite oxide catalyst according to claim 4, wherein the composite oxide catalyst has the formula $Mo_aV_bCu_cX_dY_eZ_fO_g$, wherein X represents at least one element selected from the group consisting of W and Nb, Y represents at least one element selected from the group consisting of Fe, Co, Ni and Bi, Z represents at least one element selected from the group consisting of Ti, Zr, Ce, Cr, Mn, Sb and Si, and a, b, c, d, e, f and g represent atomic ratios of the respective elements, with the proviso that when a is 12, b is from 1 to 12, c is from 0 to 6, d is from 0 to 12, e is from 0 to 100, f is from 0 to 100, and g is a numerical value determined by the oxidized states of the respective elements.

9. A method which comprises contacting an unsaturated aldehyde with molecular oxygen in the presence of the composite oxide catalyst obtained by the process as defined in claim 7 for gas phase oxidation to produce the corresponding unsaturated carboxylic acid.

10. The method according to claim 9, wherein the unsaturated aldehyde is acrolein, and the unsaturated carboxylic acid is acrylic acid.

11. The method according to claim 9, wherein the wherein the composite oxide catalyst has the formula $Mo_aV_bCu_cX_dY_eZ_fO_g$, wherein X represents at least one element selected from the group consisting of W and Nb, Y represents at least one element selected from the group consisting of Fe, Co, Ni and Bi, Z represents at least one element selected from the group consisting of Ti, Zr, Ce, Cr, Mn, Sb and Si, and a, b, c, d, e, f and g represent atomic ratios of the respective elements, with the proviso that when a is 12, b is from 1 to 12, c is from 0 to 6, d is from 0 to 12, e is from 0 to 100, f is from 0 to 100, and g is a numerical value determined by the oxidized states of the respective elements.

12. The process according to claim 1, wherein the graphite particles have an average particle diameter $D_{50}$ of from 10 to 50 μm.

* * * * *